United States Patent [19]
Patel et al.

[11] Patent Number: 5,885,619
[45] Date of Patent: *Mar. 23, 1999

[54] LARGE AREA SUBMUCOSAL TISSUE GRAFT CONSTRUCTS AND METHOD FOR MAKING THE SAME

[75] Inventors: Umesh H. Patel, W. Lafayette; Michael C. Hiles, Indianapolis; Bryan Whitson, W. Lafayette, all of Ind.; Boyle Cheng, Greely, Colo.; Stephen F. Badylak, W. Lafayette; Klod Kokini, Lafayette, both of Ind.

[73] Assignees: Purdue Research Foundation, West Lafayette, Ind.; Methodist Hospital of Indiana, Inc., Indianapolis, Ind.

[*] Notice: The term of this patent shall not extend beyond the expiration date of Pat. No. 5,711,969.

[21] Appl. No.: 931,299

[22] Filed: Sep. 16, 1997

Related U.S. Application Data

[63] Continuation of Ser. No. 418,515, Apr. 7, 1995, Pat. No. 5,711,969.

[51] Int. Cl.$^6$ .................................................. A61K 35/38
[52] U.S. Cl. .............................. 424/551; 623/11; 623/13
[58] Field of Search .............................. 424/551; 623/11, 623/13

[56] References Cited

U.S. PATENT DOCUMENTS

| | | | |
|---|---|---|---|
| 2,127,903 | 8/1938 | Bowen | 128/334 |
| 3,562,820 | 2/1971 | Braun | 3/1 |
| 4,902,508 | 2/1990 | Badylak et al. | 424/551 |
| 4,956,178 | 9/1990 | Badylak et al. | 424/551 |
| 5,275,826 | 1/1994 | Badylak et al. | 424/551 |
| 5,281,422 | 1/1994 | Badylak et al. | 424/551 |
| 5,352,463 | 10/1994 | Badylak et al. | 424/551 |
| 5,372,821 | 12/1994 | Badylak et al. | 424/551 |

FOREIGN PATENT DOCUMENTS

WO 95/06439 3/1995 WIPO .

OTHER PUBLICATIONS

"Comparison of Bovine Collagen Xenografts to Auotgrafts in the Rabbit", J.C. Tauro, et al., *Clinical Orthopaedics and Related Research* No. 266, May, 1991, pp. 271–284.

"Development of a Reconstituted Collagen Tendon Prosthesis", Jack D. Goldstein, et al., *The Journal of Bone and Joint Surgery, Incorporated* vol. 71–A, No. 8, Sep. 1989, pp. 1183–1191.

"Replacement of Dog's Aorta by Autologous Intestinal Muscle in the Infected Retroperitoneum", R. Broll, et al., *Eurp. Surg. Res.*, 18: 390–396 (1986).

"Aortic Replacement with Multi–Layer Submucosa Prostheses Made From Heterologous Small Intestine", G. Rotthoff, et al., presented at 8th Congress of the International Society of Cardiovascular Surgery, Vienna, Sep. 7–9, 1967.

"Replacement of the Abdominal Aorta by an lleum Muscle Tube in an animal Experiment", J. Huth, et al., (translation), *Thoraxchir. Vaxk, Chir.*, , 15(4): 401–407, Aug. 1967.

"Long Term Observations and Histological Studies on Yessel and Heart Wall Grafts From Small Intestine", R. Haring, et al., (translation), *Langenbecks Arch. Klin. Chir.*, 313:664–8.

"Replacement of the Abdominal Aorta With A Small–Intestine Muscle Tube In An Animal Experiment", J. Huth, (translation), *Zentralbl Chir.*, , 92 (26/2): 1817–19 (1967).

"Reconstruction of the Arterial flow path by Autologous Intestinal Muscle Grafts in The Dog", H.P. Bruch, et al., (translation), *Folia Angiologica*, vol. 29 (3–5/81) pp. 65–68.

"Replacement of the Aorta by Multiayered Submucosa Prostheses of Heterologous lleum", G. Rotthoff, et al., (translation), *Bulletin de la Societe international de Chirurgie*, No. 2 1969, 256–259.

*Primary Examiner*—Jean C. Witz
*Attorney, Agent, or Firm*—Barnes & Thornburg

[57] ABSTRACT

A unitary heterolaminar tissue graft construct is prepared by fusing partially overlapped strips or sheets of submucosa tissue. The submucosa components are fused by compressing at least the overlapped positions of said strips between two surfaces under conditions that allow or promote dehydration of the compressed submucosa sheets. Three dimensional graft constructs can be prepared by using complementary non-planar compressive surfaces.

10 Claims, No Drawings

LARGE AREA SUBMUCOSAL TISSUE GRAFT CONSTRUCTS AND METHOD FOR MAKING THE SAME

This is a continuation of application Ser. No. 08/418,515 filed Apr. 7, 1995, now U.S. Pat. No. 5,711,969.

Field of the Invention

This invention relates to tissue graft constructs useful in promoting regrowth and healing of damaged or diseased tissue structures. More particularly this invention is directed to submucosal tissue graft cbnstructs formed from multiple strips of submucosal tissue of a warm-blooded vertebrate and a method for making said constructs.

BACKGROUND AND SUMMARY OF THE INVENTION

It is known that compositions comprising the tunica submucosa delaminated from both the tunica muscularis and at least the luminal portion of the tunica mucosa of the intestine of warm-blooded vertebrates can be used as tissue graft materials. See, for example, U.S. Pat. Nos. 4,902,508 and 5,281,422. The compositions described in those patents are characterized by excellent mechanical properties, including high compliance, a high burst pressure point, and an effective porosity index which allowed such compositions to be used beneficially for vascular graft constructs and in connective tissue replacement applications. When used in such applications the submucosal graft constructs appear to serve as a matrix for the regrowth of the tissues replaced by the graft constructs. Significantly, too, in over 600 cross-species implants, submucosa-derived graft compositions have never been shown to elucidate a tissue graft rejection reaction.

One limitation of the submucosal graft constructs described in above mentioned patents is that the size of the graft is restricted by the size of the source material from which the submucosal tissue is prepared. For example, the size of a submucosal tissue graft prepared from intestinal tissues is limited by the length and circumference of the source segments intestinal tissue. Yet several applications of submucosal tissue graft constructs, including hernia repair, skin graft, meningeal coverings, repair of gastroschisis (congenital stomach defects) and organ tissue replacement, often require larger sheets of graft material than can be prepared directly from natural sources.

Large sheets of submucosal tissue can be prepared from smaller segments of submucosal tissue through conventional techniques such as weaving, knitting or the use of adhesives. However, commercial implementation of such techniques are often impractical and expensive. Additionally the use of adhesives or chemical pretreatment to promote adhesion of the tissue strips can compromise the biotropic properties of the submucosal grafts. Thus there is a need for an inexpensive, easily manufactured, large area submucosal tissue graft construct that retains its biotropic properties.

The present application is directed to a method of forming large area submucosal tissue graft constructs from vertebrate submucosa-derived matrices and the graft constructs formed by said method. Submucosa-derived matrices for use in accordance with the present invention are collagen based biodegradable matrices comprising highly conserved collagens, glycoproteins, proteoglycans, and glycosaminoglycans in their natural configuration and natural concentration. One extracellular collagenous matrix for use in this invention is submucosal tissue of a warm-blooded vertebrate. Submucosal tissue can be obtained from various sources, for example, intestinal tissue harvested from animals raised for meat production, including, pigs, cattle and sheep or other warm-blooded vertebrates. Vertebrate submucosal tissue is a plentiful by-product of commercial meat production operations and is thus a low cost tissue graft material.

Unitary heterolaminar sheets (graft constructs) of submucosal tissue are prepared in accordance with the present invention by adhering multiple partially overlapped strips of submucosal tissue to each other. The unitary sheet of tissue has a surface area larger than any one of the component submucosa strips. The present process comprises the steps of overlapping at least a portion of one strip of submucosal tissue with at least a portion of another strip of submucosal tissue and applying pressure at least to said overlapped portions under conditions allowing dehydration of the submucosal tissue. Under these conditions the overlapped portions will become "fused" to form a unitary large sheet of tissue. The large area graft constructs formed in accordance with the present invention consist essentially of submucosal tissue, free of potentially compromising adhesives and chemical pretreatments, and have a greater surface area and greater mechanical strength than the individual strips used to form the graft construct.

DETAILED DESCRIPTION OF THE PREFERRED EMBODIMENTS

There is provided in accordance with this invention a method for forming tissue graft constructs comprising large area sheets of submucosal tissue. The method comprises the steps of fusing multiple strips of submucosal tissue to form unitary heterolaminar, and optionally multi-ply sheets of submucosal tissue.

The submucosal tissue suitable for use in the formation of the present graft constructs comprises naturally associated extracellular matrix proteins, glycoproteins and other factors. One source of submucosal tissue is the intestinal tissue of a warm-blooded vertebrate. Small intestinal tissue is a preferred source of submucbsal tissue for use in this invention.

Suitable intestinal submucosal tissue typically comprises the tunica submucosa delaminated from both the tunica muscularis and at least the luminal portion of the tunica mucosa. In one embodiment of the present invention the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of submucosal tissue for use in accordance with this invention is described in U.S. Pat. No. 4,902,508, the disclosure of which is expressly incorporated herein by reference. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. A similar procedure can be used to prepare submucosa tissue from urinary bladder. The submucosal tissue is rinsed with saline and optionally sterilized; it can be stored in a hydrated or dehydrated state. Lyophilized or air dried submucosa tissue can be rehydrated and used in accordance with this invention without significant loss of its biotropic and mechanical properties.

In one embodiment of this invention, large area compliant sheets of submucosal tissue are formed from multiple partially overlapped strips of submucosal tissue. The dimensions of the individual strips of submucosal tissue used is not critical and the term "strip of submucosal tissue" is defined herein to include submucosal tissue from one or more vertebrate sources or organs in a wide variety of sizes and shapes. The method of forming large sheets of submucosal tissue comprises the steps of overlapping at least a portion of one strip of submucosal tissue with at least a portion of a second strip of submucosal tissue, and applying pressure at least to said overlapped portions under conditions allowing dehydration of the submucosal tissue. The amount of tissue overlap between the adjacent strips of submucosal tissue can be varied based on the intended use and the desired properties of the large area graft construct, provided that at least a portion of each strip of submucosal tissue overlaps with a portion of another strip of submucosal tissue. The applied pressure fuses the strips of submucosal tissue to one another along the overlapped portions, producing a compliant unitary heterolaminar sheet of submucosal tissue. The term "heterolaminar" as used herein refers to the variability in the number of layers of submucosa superimposed at (and fused) at different points on the unitary graft construct. The heterolaminar structure of the present graft constructs, especially in multi-ply constructs, provides enhanced mechanical strength.

Submucosal tissue typically has an abluminal and a luminal surface. The luminal surface is the submucosal surface facing the lumen of the organ source and typically adjacent to an inner mucosa layer in vivo whereas the abluminal surface is the submucosal surface facing away from the lumen of the organ source and typically in contact with smooth muscle tissue in vivo. The multiple strips of submucosal tissue can be overlapped with the abluminal surface contacting the luminal surface, the luminal surface contacting the luminal surface or with the abluminal surface contacting the abluminal surface of an adjacent strip of submucosal tissue. All of these combinations of overlapping strips of submucosal tissue from some or different vertebrate or organ sources will produce a large area sheet of submucosal tissue in accordance with the present invention upon compression of at least the overlapped portions under conditions allowing dehydration of the tissue.

The strips of submucosal tissue of the present invention can be preconditioned by stretching the material in a longitudinal or lateral direction as described in U.S. Pat. No. 5,275,826, the disclosure of which is expressly incorporated herein by reference. The submucosal material can be preconditional prior to the formation of the large area sheets or the submucosal tissue can be preconditioned after formation of the sheets. Preferably if the submucosal tissue is to be preconditioned, the preconditioning should be carried out prior to the formation of the large area sheet.

Pressure is applied to the overlapped portions by compressing the submucosal tissue between two surfaces. The two surfaces can be formed from a variety of materials and in any shape depending on the desired form and specification of the unitary graft construct. Typically the two surfaces are formed as flat plates but they can also include other shapes such as screens, optionally heated or perforated, opposed cylinders or rollers and complementary nonplanar surfaces. In preferred embodiments at least one of the two surfaces is water permeable. The term water permeable surface as used herein includes surfaces that are water absorbent, microporous or macroporous. Macroporous materials include perforated plates or meshes made of plastic, metal, ceramics or wood.

The submucosal tissue is compressed in accordance with one embodiment by placing the overlapped portions of the strips of submucosal tissue on a first surface and placing a second surface on top of the exposed submucosal surface. A force is then applied to bias the two surfaces towards one another, compressing the submucosal tissue between the two surfaces. The biasing force can be generated by any number of methods known to those skilled in the art and include the passage of the apparatus through a pair of pinch rollers (the distance between the surface of the two rollers being less than the original distance between the two plates), the applying a weight on the top plate, the use of a hydraulic press or the application of atmospheric pressure on the two surfaces.

In one preferred embodiment the strips of submucosal tissue are subjected to conditions allowing dehydrating of the submucosal tissue concurrent with the compression of the tissue. The term "conditions allowing dehydration of the submucosal tissue" is defined to include any mechanical or environmental condition which promotes or induces the removal of water from the submucosal tissue at least at the points of overlap. To promote dehydration of the compressed submucosal tissue, at least one of the two surfaces compressing the tissue is water permeable. Dehydration of the tissue can optionally be further enhanced by applying blotting material, heating the tissue or blowing air across the exterior of the two compressing surfaces.

The multiple strips of submucosal tissue are typically compressed for 12–48 hours at room temperature, although heat may also be applied. For example a warming blanket can be applied to the exterior of the compressing surfaces to raise the temperature of the compressed tissue up to about 40° C. to about 50° C. The overlapped portions are usually compressed for a length of time determined by the degree of dehydration of the tissue. The use of heat increases the rate of dehydration and thus decreases the amount of time the overlapped portions of tissue are required to be compressed. Typically the tissue is compressed for a sufficient time to produce a stiff but flexible material. Sufficient dehydration of the tissue is also indicated by a increase in impedance of electrical current flowing through the tissue. When impedance has increased by 100–200 ohms, the tissue is sufficiently dehydrated and the pressure can be released.

The compressed submucosal tissue can be removed from the two surfaces as a unitary compliant large area tissue construct. The construct can be further manipulated (i.e. cut, folded, sutured, etc.) to suit various medical applications where the submucosal material of the present invention is required.

A vacuum can optionally be applied to submucosal tissue during the compression procedure. The applied vacuum enhances the dehydration of the tissue and may assist the compression of the tissue. Alternatively the application of a vacuum may provide the sole compressing force for compressing the overlapped portions of the multiple strips of submucosal tissue. For example the overlapped submucosal tissue is laid out between two surfaces, preferable one of which is water permeable. The apparatus is covered with blotting material, to soak up water, and a breather blanket to allow air flow. The apparatus is then placed in a vacuum chamber and a vacuum is applied, generally ranging from 14–40 inches of Hg. Optionally a heating blanket can be placed on top of the chamber to heat the submucosal tissue during the compression of the tissue. Chambers suitable for use in this embodiment are known to those skilled in the art and include any device that is equipped with a vacuum port. The resulting drop in atmospheric pressure coacts with the two surfaces to compress the submucosal tissue and simultaneously dehydrate the submucosal tissue.

The present method is also used to produce multilayered large area sheets of submucosal tissue. In one embodiment, the multilayered sheets of the present invention are formed by overlapping a portion of one strip of submucosal tissue with a portion of another strip of submucosal tissue to form a first layer. The size and physical properties of the first layer of the submucosal tissue can be regulated by the number of overlapped strips of submucosal tissue and the percent of the overlapped portion of each strip. Additional strips of submucosal tissue are then overlaid onto the overlapped portions of the first layer to form a second layer, wherein the edges of the additional strips are optionally a an acute angle to the edges of the strips in the first layer, and wherein said formed second layer is coplanar with the first layer. The strips of submucosal tissue of the second layer can be positioned so that at least a portion of one strip of submucosal tissue of the second layer overlaps with at least a portion of another strip of submucosal tissue of the second layer. Additional strips of submucosal tissue can be overlaid on the overlapped portions of the first and second layers to provide additional layers of submucosal tissue. The multiple layers of submucosal tissue are then compressed under dehydrating conditions to form a multi-ply heterolaminar submucosal tissue construct having a surface area greater than any one of the individual strips of submucosal tissue used to form the multilayered sheet.

In one embodiment of the present invention submucosal tissue is cut to into strips, each strip having generally parallel sides, and used to form the multilayered heterolaminar sheets of the present invention. In this embodiment the strips of submucosal tissue of the second layer are overlaid onto the overlapped portions of the first layer such that the edges of the first layer submucosal strips are at an angle relative to the edges of the second layer submucosal strips. The overlapped portions of submucosal tissue are compressed under dehydrating conditions to form the multilayered heterolaminar sheet. These sheets can be cut without unraveling and do not delaminate when soaked in water for a period of time (greater than one hour) that corresponds to the time required for implanting the sheet in a host. If the sheet is properly implanted such that it is sutured on all sides, delamination should not occur subsequent to implantation.

In one embodiment, after multiple strips of submucosal tissue are overlapped with one another, the overlapped portions are manipulated to remove trapped air and bulk quantities of water prior to fusing the strips into a single sheet of submucosal tissue. In general the trapped air bubbles and bulk quantities of water are squeezed out through the use of a compressing force which is moved across the surface of the overlapped portions. The compressing force can take the form of a cylinder that is rolled across the-surface of the overlapped portions, or alternatively the overlapped portions can be passed between two or more rollers wherein the distance between the surface of the opposing rollers is less than the thickness of the submucosal sheet. The overlapped portions can then be compressed if necessary for an additional length of time under dehydrating. conditions to fuse the multiple strips into a single sheet of submucosal tissue in accordance with the present invention.

The mechanical properties of the submucosal sheets prepared in accordance with the present invention can be tailored to the medical application needs by adjusting the number of layers in the sheet, varying the angle of adjacent layers to each other, changing the water permeability of the compressing surfaces and/or the composition of the compressing surfaces, selecting the shape of the compressive surfaces, and varying the load applied to press the submucosal strips into a large area submucosal sheet. optionally the large area tissue grafts of the present invention can be formed into various shapes for tissue graft applications. For example, in organ reconstruction applications the large area sheets can be formed in the shape of a hollow sphere or pouch. Such a shaped construct would be advantageous in the replacement of large regions of the urinary bladder or stomach. These shaped submucosal tissue constructs can be formed by conventional techniques such as cutting and suturing the tissue to form a desired shape.

Strips of submucosal tissue can be formed into a large sheet of submucosal tissue having a nonplanar shape through a simple manufacturing procedure. The method comprises the steps of placing multiple strips. of submucosal tissue between two complementary nonplanar shaped surfaces and compressing overlapped strips of submucosal tissue between the two surfaces. The complementary shaped surfaces are formed such that the two surfaces can be pressed together such that the surfaces fit snug against one another without leaving any substantial pockets of air between the two surfaces. Preferably at least one of the two complementary surfaces is water permeable.

One method of forming a shaped submucosal construct comprises placing multiple strips of submucosal tissue on a nonplanar shaped porous surface such that the submucosal tissue conforms to the shape of the porous surface. Preferably the submucosal tissue is placed on the porous surface without stretching the material, however, the submucosal tissue can be stretched to facilitate covering the shaped porous surface. Each of the strips of submucosal tissue is positioned on the porous surface to overlap at least a portion of an adjacent strip of submucosal tissue. The overlapping portions of the submucosal tissue are then covered with a second shaped surface that is complementary in shape with the first porous surface and pressure is applied to compress the submucosal tissue between the two surfaces under conditions allowing dehydration of the submucosal tissue.

Alternatively the large area sheets of the present invention can be shaped into a nonplanar shape by stretching the large area sheet through the use of a die press procedure, wherein the submucosal tissue is pressed into a nonplanar shape by a porous die under dehydrating conditions such that the formed tissue graft holds its shape. Preferably a multilayered large area sheet is used in such a procedure.

EXAMPLE 1

Submucosal tissue was prepared from vertebrate intestinal tissue in accordance with the procedure described in U.S. Pat. No. 4,902,508. Strips of submucosal tissue were formed from a segment of intestinal tissue of a warm-blooded vertebrate, said segment comprising the tunica submucosa delaminated from both the tunica muscularis and at least the luminal portion of the tunica mucosa of said segment of intestinal tissue. The segment of intestinal tissue was cut along the longitudinal axis of the segment and laid flat. The tissue was then further sliced into a series of strips each having generally parallel sides.

Multiple strips of submucosal tissue were organized on a 12 by 12 inch perforated stainless steel plate wherein a portion of one strip of submucosal tissue overlaps a portion of the adjacent strip of submucosal tissue. A second 12 by 12 inch perforated stainless steel plate was then placed on top of the submucosal tissue. The perforated stainless steel plates used in this embodiment has 0.045 inch perforations arranged straight center and located 0.066 inches apart. A 50–100 pound weight was placed on top of the second stainless steel plate and the tissue was compressed for 24 hours at room. temperature.

EXAMPLE 2

Strips of submucosal tissue were prepared as described in Example 1. Multiple strips of submucosal tissue were laid out between two perforated, stainless steel plates so that a portion of one strip of submucosal tissue overlapped a portion of the adjacent strip of submucosal tissue. The "plate-submucosa-plate" apparatus was placed on a flat surface and covered with blotting material, to soak up water, and a breather blanket to allow air flow. The apparatus was then sealed into a nylon bag that has a vacuum port. A vacuum was applied (greater than 28 inches of Hg) to pull air out of the vacuum bag and the resulting drop in atmospheric pressure simultaneously compressed and dehydrated the submucosal tissue. After 24 hours of applying a vacuum, the produced sheet was moist and very flexible. No seams from the layering of the submucosal tissue were visible and the strength of a prototype 8-thickness sheet as determined by ball burst test was 80 pounds.

EXAMPLE 3

Strips of submucosal tissue were prepared as described in EXAMPLE 1. The submucosal tissue strips were organized on a mesh so that a portion of one strip of submucosal tissue overlapped a portion of the adjacent strip of submucosal tissue. Once the mesh was covered with one layer of submucosal tissue a second layer of submucosal tissue was applied on top of the first layer so that the edges of the submucosal strips of the second layer were at an angle relative to edges of the submucosal strips of the first layer.

After all the strips of submucosal tissue were placed on the mesh, another mesh was placed on top of the submucosal tissue layers and the "mesh-submucosal tissue-mesh" sandwich was compressed with a load and dried. This process produced a dried large area submucosal sheet that was pealed off the mesh as a unitary graft construct.

We claim:

1. A method for forming a unitary tissue graft construct consisting essentially of multiple strips of submucosal tissue, said construct having a surface area greater than any one of the individual strips used to form said construct, said method comprising the steps of overlapping a portion of one strip of submucosal tissue with a portion of a second strip of submucosal tissue and compressing at least the overlapped portions between two surfaces, at least one of which is water permeable, under dehydrating conditions.

2. The method of claim 1, further comprising the step of applying a vacuum to the submucosal tissue during compression thereof.

3. The method of claim 2, wherein the applied vacuum coacts with the two surfaces to compress the submucosal tissue.

4. The method of claim 1, further comprising the step of applying heat to the submucosal tissue during compression thereof.

5. The method of claim 1, wherein both surfaces are water permeable.

6. The method of claim 1, wherein the two surfaces are complementary nonplanar surfaces wherein compression between the two surfaces produces a tissue graft construct shaped to conform to those surfaces.

7. The method of claim 1, wherein the submucosal tissue is intestinal submucosa comprising the tunica submucosa delaminated from both the tunica muscularis and at least the luminal portion of the tunica mucosa.

8. The method of claim 1 farther comprising the step of moving a compressing force across the surface of the construct to remove air and bulk water trapped between the overlapped strips before compressing the overlapped portions between the two surfaces.

9. The method of claim 8, wherein the two surfaces comprise a pair of opposed rollers and the overlapped strips are passed between the rollers.

10. A large area multi-laminate sheet of submucosal tissue comprising multiple strips of intestinal submucosal tissue delaminated from both the tunica muscularis and at least the lurninal portion of the tunica mucosa of a warm blooded vertebrate, said strips having an abluminal surface and a lurinal surface, wherein each strip is partially overlapped with at least one additional strip of submucosal tissue and the the luminal surface of each strip is in contact with the abluminal surface of at least one additional strip of submucosal tissue, said multiple strips of intestinal submucosa tissue being fused to one another by compressing the strips under dehydrating conditions to form a sheet of submucosal tissue having a surface area greater than any one of the individual strips used to form said construct.

* * * * *